(12) United States Patent
Antelman

(10) Patent No.: US 6,258,385 B1
(45) Date of Patent: Jul. 10, 2001

(54) TETRASILVER TETROXIDE TREATMENT FOR SKIN CONDITIONS

(75) Inventor: Marvin S. Antelman, Pehovot (IL)

(73) Assignee: Marantech Holding, LLC, Providence, RI (US)

( * ) Notice: Subject to any disclaimer, the term of this patent is extended or adjusted under 35 U.S.C. 154(b) by 0 days.

(21) Appl. No.: 09/552,172

(22) Filed: Apr. 18, 2000

Related U.S. Application Data

(63) Continuation-in-part of application No. 09/296,998, filed on Apr. 22, 1999, now abandoned.

(51) Int. Cl.⁷ ............................. A61K 33/38; A61K 9/00
(52) U.S. Cl. .................. 424/618; 424/405; 424/439; 514/859; 514/861; 514/863; 514/925; 514/928; 514/931; 514/934; 514/937; 514/938; 514/969
(58) Field of Search ..................... 424/405, 489, 424/618; 514/859, 861, 863, 925, 928, 931, 934, 937, 938, 969

(56) References Cited

U.S. PATENT DOCUMENTS

| | | | |
|---|---|---|---|
| 4,828,832 | * 5/1989 | De Cuellar et al. | 424/618 |
| 5,017,295 | 5/1991 | Antelman | 210/764 |
| 5,073,382 | 12/1991 | Antelman | 424/604 |
| 5,078,902 | 1/1992 | Antelman | 210/764 |
| 5,089,275 | 2/1992 | Antelman | 424/602 |
| 5,098,582 | 3/1992 | Antelman | 210/759 |
| 5,211,855 | 5/1993 | Antelman | 210/758 |
| 5,223,149 | 6/1993 | Antelman | 210/764 |
| 5,334,588 | * 8/1994 | Fox, Jr. | 514/171 |
| 5,336,416 | 8/1994 | Antelman | 210/764 |
| 5,336,499 | 8/1994 | Antelman | 424/405 |
| 5,571,520 | * 11/1996 | Antelman | 424/405 |
| 5,676,977 | 10/1997 | Antelman | 424/618 |
| 5,772,896 | 6/1998 | Denkewicz, Jr. et al. | 210/754 |

OTHER PUBLICATIONS

The Merck Manual (16th Ed. 1992), 'Dermatologic Disorders', pp. 2399–2460.*
Dorland's Illustrated Medical Dictionary (28th Ed. 1994), pp. 351,759–60.*
Remington's Pharmaceutical Sciences (17th Ed. 1985), pp. 1573–1575, 1585–1602.*
Antelman, Marvin S.; "Silver (II,III) Disinfectants"; *Soap/Cosmetics/Chemical Specialties*, Mar. 1994, pp. 52–59.
Antelman, Marvin S.; *Abstracts of the American Chemical Society*; 1992(203).
Antelman, Marvin S.; "Anti–Pathogenic Multivalent Silver Molecular Semiconductors"; *Precious Metals*; 1992(16); pp. 141–149.
Antelman, Marvin S.; "Multivalent Silver Bactericides"; *Precious Metals*; 1992(16); pp. 151–163.

* cited by examiner

Primary Examiner—Jose' G. Dees
Assistant Examiner—Frank Choi
(74) Attorney, Agent, or Firm—Pennie & Edmonds LLP

(57) ABSTRACT

The invention relates to the use of electron active molecular crystals comprising tetrasilver tetroxide ($Ag_4O_4$) for the treatment and cure of dermatological skin conditions (diseases) ranging from dermatitis, acne and psoiasis to herpes and skin ulcers.

20 Claims, No Drawings

TETRASILVER TETROXIDE TREATMENT FOR SKIN CONDITIONS

This Application is a Continuation-In-Part of application Ser. No. 09/296,998, filed Apr. 22, 1999, now abandoned.

BACKGROUND OF THE INVENTION

The present invention relates to the use of electron active molecular crystals comprising tetrasilver tetroxide ($Ag_4O_4$) for the treatment and cure of dermatological conditions or diseases.

The present invention is related to concepts previously elucidated and disclosed in U.S. Pat. No. 5,336,499 (1994); U.S. Pat. No. 5,571,520 (1996) and U.S. Pat. No. 5,676,977 (1997). Said concepts have also been published in an article entitled "Silver (II, III) Disenfectants" (*Soap/Cosmetics/Chemical Specialties,* 1994; March, pp. 52–59).

The aforementioned references disclose that said tetrasilver tetroxide devices kill and/or inhibit a wide variety of pathogens ranging from gram positive and negative bacteria (e.g., *E coli* and *Staphylococcus aureus*), algae and mold (e.g., Chorella and *Candida albicans*) and the AIDS virus. Said references also contain detailed descriptions of the mechanism via which said molecular crystal devices operate. The instant inventor also presented his subsequent results and concepts at a Seminar entitled "Incurable Diseases Update" (Weizmann Institute of Science, Rehovot, Israel, Feb. 11, 1998). The title of his presentation was "Beyond Antibiotics, Non Toxic Disinfectants and Tetrasil Mademark of applicant for the tetroxide)".

In the aforecited article it was shown that the effects of the electron transfer involved with respect to the tetroxide, phenomenally, rendered it a more powerful germicide than other silver entities. The instant inventor holds patents for multivalent silver anti microbials, e.g., U.S. Pat. No. 5,017,295 for Ag(II) and U.S. Pat. No. 5,223,149 for Ag (III); and while these entities are stronger anti microbials than Ag (I) compounds they pale by comparison to the tetroxide and so does colloidal silver which derives its germicidal properties from trace silver (I) ions it generates in various environments. Accordingly, the oligodynamic properties of these entities may be summarized as follows, which is referred to as the Horsfal series:

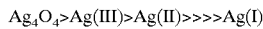

$Ag_4O_4 > Ag(III) > Ag(II) >>>> Ag(I)$

The other unique property of the tetroxide was that it did not stain organic matter such as skin in like manner as Ag(I) compounds do. In addition, it was light stable.

The main object of this invention is to utilize tetrasilver tetroxide molecular devices to cure dermatological diseases or conditions.

Another object of this invention is to use tetrasilver tetroxide molecular devices to control those dermatological conditions or diseases which cannot be cured completely by said devices.

Still another object of this invention is to use tetrasilver tetroxide molecular devices to reduce the time of affliction of dermatological conditions or diseases.

Still another object of this invention is to utilize said devices in the aforesaid dermatological applications without staining the skin.

SUMMARY OF THE INVENTION

This invention relates to a molecular scale device comprising a single crystal of tetrasilver tetroxide ($Ag_4O_4$). Several trillion of these molecules may be employed in various pharmaceutical formulations and therapies to effectuate the treatment and cure of various dermatological conditions and diseases. These conditions and diseases vary and include eczema, psoriasis, dermatitis, disease induced skin ulcers, undefined tropical diseases, shingles, rashes, bedsores, cold sores, blisters, boils, herpes simplex, acne, pimples, skin chafing, cracking, itchiness, skin peeling, and warts.

More particularly, the invention relates to a method for treating dermatological skin disease comprising applying a composition comprising tetrasilver tetroxide directly to the affected skin areas, said composition being free of added oxidizing agent.

Even more particularly, the invention relates to a method for treating dermatological skin conditions selected from the group consisting of eczema, psoriasis, dermatitis, ulcers, shingles, rashes, bedsores, cold sores, blisters, boils, herpes, acne, pimples, skin chafing, cracking, skin itch, skin peeling and warts comprising applying tetrasilver tetroxide directly to the affected skin area.

DESCRIPTION OF THE INVENTION

The crystal lattice of the $Ag_4O_4$ molecular device operates against pathogens by transferring electrons from its two monovalent silver ions to the two trivalent silver ions in the crystal contributing to the death of pathogens by traversing their cell membrane surface. This in effect "electrocutes" the pathogens. The electrons are forced out of their balanced crystals by such labile groups as NH, $NH_2$, S—S and SH comprising pathogen cell membrane surface. However, normal cells will not be affected because they do not proliferate fast enough to expose these labile bonds.

The $K_A$ of $Ag_4O_4$ is $7.9 \times 10^{-13}$, therefore the molecule will not be disturbed unless more stable complexes are formed with such ligands as those comprising the pathogen cell membrane surface in a dynamic state. Indeed the end result of the electron transfer, which is a redox reaction, results in the monovalent Ag ions being oxidized to Ag(II) and the trivalent Ag ions being reduced to the same end product, Ag(II). Accordingly, the well-known affinity for monovalent silver for certain elements such as sulfur and nitrogen is far exceeded here, for divalent silver will not merely bind to these elements as does silver, but will actually form chelate complexes with their ligands. The molecular crystal attraction for the cell membrane surfaces is thus driven by powerful covalent bonding forces.

The electron transfer can be depicted by the following redox half reactions:

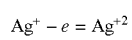

$Ag^+ - e = Ag^{+2}$

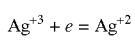

$Ag^{+3} + e = Ag^{+2}$

It was found by rigorous testing that silver tetroxide was comparatively non toxic. Since said oxide was effective at PPM concentrations in killing pathogens, commercial concentrates were formulated with 2% of the tetroxide. For acceptance of said oxide in commerce for which an EPA registration number was obtained (no. 3432-64), it was necessary for the oxide to undergo a series of toxicity tests, for which a 3% concentrate was used and evaluated by a certified laboratory employing good laboratory practice (GLP) according to the Code of Federal Regulations.

The results were as follows:

| | |
|---|---|
| Acute Oral Toxicity | $LD_{50}$ Greater than 5,000 mg./Kg. |
| Acute Dermal Toxicity | $LD_{50}$ Greater than 2,000 mg./Kg. |
| Primary Eye Irritation | Mildly irritating |
| Primary Skin Irritation | No irritation |
| Skin Sensitization | Non Sensitizing |

Subsequent evaluations showed that unless persons were prone to silver allergies, the pure tetroxide could be applied to the skin without any ill effects or evidence of irritation, despite the fact that said oxide is a powerful oxidizing agent. This can perhaps be explained by its stability manifested by its aforecited $K_A$.

It was previously postulated in earlier patents relating to the various uses of the oxide that it was required to use it in combination with an excess of strong oxidizing agent such as a persulfate in order to effectively kill pathogens. However, the additional presence of oxidizing agent tends to be irritating to the skin. It has been found in accordance with the present invention that the additional oxide is unnecessary and in fact undesirable for the purpose of treating the skin diseases described herein. Therefore, the present invention contemplates application of the oxide to the skin in the absence of the additional oxidizer and the use of formulations which are free of added additional oxidizing agent such as a persulfate.

A preferred mode of application of the oxide of the invention is as a topical agent, either directly as a powder or in non-sprayable or sprayable form. Non-sprayable forms can be semi-solid or solid forms comprising a carrier indigenous to topical application and having a dynamic viscosity preferably greater than that of water. Suitable formulations include, but are not limited to, suspensions, emulsions, creams, ointments, powders, liniments, salves and the like. If desired, these may be sterilized or mixed with auxiliary agents, e.g., thixotropes, stabilizers, wetting agents, and the like. Preferred vehicles for non-sprayable topical preparations include ointment bases, e.g., polyethylene glycol-1000 (PEG-1000); conventional ophthalmic vehicles; creams; and gels, as well as petroleum jelly and the like. These topical preparations may also contain emollients, perfumes and/or pigments to enhance their acceptability for various usages.

Where the oxide is applied to the skin combined with a carrier such one or more of the carriers described above, it may be combined with the carrier at a level of from about 50 to 250,000 PPM, more preferably from about 400 to 50,000 PPM, based on the weight of the carrier, and applied to the skin 1 to 3 times per day until the condition is cured or satisfactorily controlled. Generally, the composition may be applied at a dosage level of from about 10 to 500 mg per cm$^2$ of skin surface.

Accordingly, the oxide was used directly in powder form as well as in several compounded formulations for treating a wide assortment of skin conditions and diseases. Success was achieved in all cases except for certain stubborn nail fungi. After much experimenting it was found that the best carrier for a commercial product was white petroleum jelly.

Other objects and features of the present invention shall become apparent to those skilled in the art when the present invention is considered in view of the accompanying examples. It should, of course, be recognized that the accompanying examples illustrate preferred embodiments of the present invention.

EXAMPLE 1

A female, age 28, resident of Central America, had a red rash caused by an unidentified dermatological tropical disease on her thigh. The condition was cured by a light dusting of $Ag_4O_4$ crystals on the area. Similar occurrences in the past to the subject failed to be cured by other dermatological preparation sold as cures for said condition.

EXAMPLE 2

A female, age 27, had a fungus infection in her navel. She was cured by direct application of $Ag_4O_4$ to the affected area within 24 hours.

EXAMPLE 3

A female in her early thirties had suffered from recurrent cold sores for five years. The subject stated in a written communication, "I have tried every over-the-counter medication for this ailment without even marginal success. I even tried the five times a day for five days herpes medication that my doctor prescribed with disappointing results." Subject tried various concentration of $Ag_4O_4$ dispersed in petroleum jelly. All formulation improved the severity and duration of the herpes simplex. Subject was given a final formulation of 10,000 PPM $Ag_4O_4$ dispersed in white petroleum jelly. In many instances quick application of the ointment resulted in disappearance of the cold sore the next day. Otherwise if not caught quickly the sore could be contained within 36 hours which was a vast improvement over the previous treatments.

EXAMPLE 4

An 82-year-old female had suffered six months from an external vaginal itch which defied treatment. Application of $Ag_4O_4$ ointment (as described in Example 3) cured the condition.

EXAMPLE 5

Twenty-two samples of $Ag_4O_4$ ointment were distributed to individuals who were suffering from the herpes simplex. They all applied the ointment. While there was no attempt made to record the exact condition of the herpes subjects, all 22 cases were cured within 48 hours.

EXAMPLE 6

Having achieved success against herpes simplex, it was decided to test $Ag_4O_4$ ointment against shingles which is caused by herpes zoster. Accordingly, a 67-year-old male applied the ointment three times a day for two days, after which time the shingles condition was completely gone.

EXAMPLE 7

Two individuals, one male, the other female, ages 33 and 48, who were suffering from external acne condition, treated their skin three times a day with $Ag_4O_4$ ointment. They were completely cured after two days of applying the ointment.

EXAMPLE 8

Fifteen patients with an age ranging from 30 to 35 which were diagnosed as having oral viral herpes were arranged in two groups. Group I consisted of five patients which suffered from severe oral viral outbreaks with a recurring frequency of 21–28 days. The sizes of the herpes sores ranged from 3.5–5.0 mm. Group II consisted of ten patients who suffered from normal oral viral outbreaks with a recurring frequency of 28–42 days. The sizes of the herpes sores ranged from 1.25–1.75 mm. Both groups applied tetrasilver tetroxide ointment to the effected areas with 50–200 mg. of ointment containing 3% tetrasilver tetroxide. Group I applied the ointment (within 12 hrs.) after the herpes sores broke through the skin and blistered. Group II was divided into two subgroups. Group IIA applied the ointment (within 12 hrs.) after the herpes sores broke through the ski and blistered. Group IIB applied the ointment 4–12 hrs. before the herpes sores broke through the skin and blistered. Application was twice daily. Patients reported daily on the pharmacological effects. Sizes of the herpes growth were observed on a daily basis for five days and frequency of reoccurrence was recorded.

Summary of Results

Group I: Over a period of 24–48 hours all of the patients observed the herpes sore regress and dry out. By day three the sores were not visible and the skin was healed. All patients exhibited a longer recurrence time from 32–44 days excluding one patient who did not have a recurrence for eight months. The sizes of the herpes upon recurrence were significantly smaller at 2.2–3.5 mm.

Group IIA: Over a period of 24–48 hours all the patients observed the herpes sore regress and dry out. By the end of day the sores were not visible and the skin was healed. All patients exhibited a longer recurrence time from 34–55 days. The sizes of the herpes upon reoccurrence were significantly smaller at 0.8–1.4 mm.

Group IIB: Over a period of 12–24 hours all the patients observed that the herpes sore was retained and never broke through the skin as a blister. By the end of day two there were no signs of the herpes sore at all. There was not even the slightest amount of discomfort around the area where the blisters would have flourished. All patients exhibited a longer recurrence time from 36–62 days. The sizes of the herpes upon recurrence were 0.7–1.6 mm.

Conclusions

Tetrasilver tetroxide used as a topological ointment:

1. Eliminates oral viral herpes sores within a period of 48 hours from the time of the first application.
2. Extends the recurrence period of the viral herpes breakout cycle.
3. Prevents the herpes virus from breaking through the skin when used before an outbreak occurs.

EXAMPLE 9

Twenty eight patients in the age group ranging from 45 to 65 presenting with diabetes—induced foot ulcers were arranged in two groups. All of the patients were taking insulin injections and were diagnosed as Type I insulin dependent.

Group I consisted of fourteen patients where culture swabs of the ulcerated skin indicated the presence of bacteria (infection). Group II consisted of fourteen patients where culture swabs of the ulcerated skin did not indicate the presence of abnormal amounts of bacteria, (no infection).

The patients in each group were treated by applying 200 mg of a petroleum jelly containing 3 wt % tetrasilver tetronide twice daily to the ulcerated sores for a 30 day period. Daily evaluations of the skin condition were conducted by a dermatologist.

Summary of Results

Group I: Within 48 hours of the onset of treatment the sores on the feet of all patients began to dry out. After 72 hours, the ulcers on all patients started to heal at the borders. By the fourth day, inflammation of the diseased tissue eased and by the sixth day the ulcers were completely dry with no surface secretions. By the tenth day the ulcers on all patients had completely disappeared. Lab tests indicated no sign of infection on the feet of any patient.

Group II: Within 24 hours of the onset of treatment the sores on the feet of all patients began to dry out and heal at the borders with no secretion. By the third day the sores on all patients were covered with new healthy tissue. By the tenth day the ulcers had healed and completed the process of forming scar tissue by 80%. At day 14 of the treatment all of the ulcers were 100% healed with no sign of infection.

Continuous monitoring of both groups over the 30 day period indicated no reappearance of the ulcers.

The above testes demonstrate that tetrasilver tetroxide treatment is effective in both curing infections associated with diabetes-induced ulcers and in healing the ulcers themselves. The tetroxide accelerated the neovascularization' process of the affected tissue.

EXAMPLE 10

Twenty patients ranging from age 8 months to 12 years were clinically diagnosed as suffering from atopic dermatitis involving inflamed lesions of the face and extremities, but without bacterial involvement. These patients were previously treated by the application of topical steroids to the affected skin areas, which was discontinued. The patients were divided into two groups.

Group I consisted of ten randomly selected patients. A petroleum jelly containing 3 wt % tetrasilver tetroxide was applied at a dosage of about 100 mg. to all affected skin areas of each patient twice daily for a period of days. Daily evaluation of the skin condition was made by a dermatologist.

Group II consisted of a control group comprising the remaining ten patients. This group was treated by twice daily application of about 100 mg of pure petroleum jelly which was free of added tetrasilver tetroxide to the affected skin areas.

Summary of Results

Group I: Within 12 hours of the onset of treatment the lesions on all patients began to show healing and drying and no longer exhibited prurito in the affected skin areas. Within 24 hours of the onset of treatment, signs of irritation of the skin areas had subsided and after 24 hours signs of irritation had disappeared and the lesions were no longer visible. Treatment on all patients was discontinued after 5 days, but the group was assessed daily for any recurrence of the lesions. Two of the patients presented a reappearance of lesions by the twenty-fourth day, but these lesions were smaller and less irritating than the original lesions. Treatment was resumed on these two patients and after 24 hours the lesions had disappeared.

Group II: At 12 hours after the onset of the application of pure petroleum jelly to the affected skin areas there were no signs of improvement of the skin. Over the next 23 day period the lesions gradually became more irritated with no sign of healing of the atopic dermatitis.

The above tests demonstrate that the tetrasilver tetroxide treatment is effective in most patients in healing atopic dermatitis within 24 hours of the commencement of treatment and appears to halt the self immunological reaction of atopic dermatitis at the local level. It is also effective in reversing disease when it recurs, increasing the period of recession of the condition.

EXAMPLE 11

Twenty four patients between the ages of 13 and 40 years were diagnosed as suffering from psoriasis, exhibiting irritation, scaliness and both the Auspitz sign and the Koebner phenomenon. All patients had been previously treated with topical steroids. The patients were divided into two groups.

Group I consisted of 12 patients where psoriasis was diagnosed less than 60 days prior to treatment A petroleum jelly containing 3 wt % tetrasilver tetroxide was applied to affected skin areas twice a day over a 30 day period and each patient was evaluated twice daily by a dermatologist.

Group II consisted of 12 patients who were diagnosed more than 60 days prior to treatment. Disease in this group was more severe than Group I and most had been suffering from psoriasis for many years, exhibiting extensive disease on their backs. This group was treated by the same protocol as Group I and was evaluated three times daily by a dermatologist.

Summary of the Results

Group I: By the tenth day of treatment the psoriatic plates and inflamed areas of the treated skin started to heal. By the twentieth day the Auspitz sign had disappeared on all patients. By day 27 the psoriatic plates present in the diseased skin of all patients had disappeared. By day 35 the skin on all patients appeared to be healed and the pigmentation process of the skin had been initiated.

Group II: By the twentieth day of treatment, the healing process on all patients had commenced as evidenced by the reduction of psoriatic plates and appearance of new tissue. By day 28 the diseased areas were of smaller sizes and the Auspitz sign was no longer visible. By day 30, the Koebner phenomenon had disappeared on all patients. By day 35, the psoriatic plates were barely visible on all patients.

Continued observation of both groups showed no further changes in their condition after treatment was halted.

The above tests demonstrate that topical application of tetrasilver tetroxide to the affected skin areas of psoriasis sufferers effectively heals and/or controls this disease.

EXAMPLE 12

Twelve Caucasian patients between the ages of 45 to 65 presented with infected bleeding skin ulcers associated with diagnosed Rabdomiosarcoma, which had persisted up to 7 months prior to treatment. The patients were divided into two groups:

Group I: Seven patients where the ulcerated lesions averaged 9 cm long and 12 cm in diameter.

Group II: Five patients where the ulcerated lesions were greater than 12 cm×2 cm.

The patients of each group were treated by the application to affected skin areas of about 200 mg of petroleum jelly containing 3 wt % of tetrasilver tetroxide three times daily over a period of 30 days.

All patients were examined daily by a dermatologist to evaluate the effectiveness of the treatment.

Summary of Results

Group I: All patients experienced a commencement of healing of the ulcers by day 27 from the start of the treatment. By day 30 the ulcers were dry. On day 40 new cells had replaced infected cells. By day 45 ulcers and sores were no longer visible and new tissue was evident replacing the ulcerated tissue.

Group II: All patients showed a commencement of the healing of the ulcers by day 28 from the start of the treatment. By day 40 the ulcers had almost disappeared and a biopsy confirmed that 80% of the diseased tissue had been replaced with healthy tissue. From a clinical standpoint, the ulcers were no longer visible.

The tests demonstrate that the topical application of tetrasilver tetroxide is effective in curing infections and healing skin ulcers associated with Rabdomiosarcoma, and without side effects.

Based on all of the test data described above, the healing mechanism associated with the use of tetrasilver tetroxide to treat and cure at least some skin diseases appears to be more than simply the killing of pathogens and curing infections which tend to aggravate disease and retard the natural healing process. The data indicate that healing is brought about even in cases where no abnormal bacteria counts or infection is evident. This suggests that tetrasilver tetroxide perhaps also acts against autoantibodies which trigger autoimmune reactions associated with diseased tissue.

What is claimed is:

1. A method for treating dermatological skin disease comprising applying a composition comprising a therapeutically effective amount of tetrasilver tetoxide directly to the affected skin of a patient in need of treatment, said composition being free of added oxidizing agent, wherein the dermatological skin disease is selected from the group consisting of eczema, psoriasis, dermatitis, ulcers, shingles, rashes, bedsores, cold sores, blisters, boils, herpes, acne, pimples, warts, and a combination thereof.

2. The method of claim 1, wherein the tetrasilver tetoxide is dispersed in a carrier medium at a concentration of from about 50 to 250,000 wt PPM, based on the weight of said carrier medium.

3. The method of claim 2 wherein said concentration is from about 400 to 50,000 PPM.

4. The method of claim 2 wherein said carrier medium comprises petroleum jelly.

5. The method of claim 1, wherein said skin disease includes cold sores.

6. The method of claim 1, wherein said skin disease includes herpes.

7. The method of claim 1, wherein said skin disease includes shingles.

8. The method of claim 1, wherein said skin disease includes acne.

9. The method of claim 1, wherein said skin disease includes psoriasis.

10. The method of claim 1, wherein said skin disease includes dermatitis.

11. The method of claim 1, wherein said skin disease includes disease-induced skin ulcers.

12. The method of claim 1, wherein said skin disease includes eczema.

13. The method of claim 1, wherein said tetrasilver tetroxide is applied in powered form.

14. The method of claim 1, wherein said composition is applied to the skin at a dosage level of from about 10 to 500 mg per $cm^2$ of skin surface.

15. The method of claim 1, wherein said skin disease includes warts.

16. The method of claim 1, wherein said skin disease includes pimples.

17. The method of claim 1, wherein said skin disease includes blisters.

18. The method of claim 1, wherein said skin disease includes bedsores.

19. The method of claim 1, wherein said skin disease includes rashes.

20. The method of claim 1, wherein said composition is applied in non-sprayable form.

\* \* \* \* \*